US00PP24251P2

(12) United States Plant Patent
Wood

(10) Patent No.: US PP24,251 P2
(45) Date of Patent: Feb. 18, 2014

(54) ***VIBURNUM* PLANT NAMED 'SPIRO'**

(50) Latin Name: *Viburnum carlesii*
Varietal Denomination: Spiro

(75) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 89 days.

(21) Appl. No.: 13/506,504

(22) Filed: Apr. 23, 2012

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — C. A. Whealy

(57) ABSTRACT

A new and distinct cultivar of *Viburnum* plant named 'Spiro', characterized by its upright and somewhat outwardly spreading plant habit; vigorous growth habit; freely branching habit; red purple-colored flower buds; numerous strongly fragrant light pink to white-colored flowers; and good garden performance.

2 Drawing Sheets

Botanical designation: *Viburnum carlesii.*
Cultivar denomination: 'SPIRO'.

BACKGROUND OF THE INVENTION

The present invention relates to a new and distinct cultivar of *Viburnum* plant, botanically known as *Viburnum carlesii* and hereinafter referred to by the name 'Spiro'.

The new *Viburnum* plant is a product of a planned breeding program conducted by the Inventor in Grand Haven, Mich. The objective of the breeding program is to develop new fragrant *Viburnum* plants with unique and attractive foliage and flower coloration.

The new *Viburnum* plant originated from an open-pollination in 1999 of an unnamed selection of *Viburnum carlesii*, not patented, as the female, or seed, parent with an unknown selection of *Viburnum carlesii*, not patented, as the male, or pollen, parent. The new *Viburnum* plant was discovered and selected by the Inventor in 2009 as a single flowering plant from within the progeny of the stated open-pollination in a controlled environment in Grand Haven, Mich.

Asexual reproduction of the new *Viburnum* plant by softwood cuttings in a controlled environment in Grand Haven, Mich. since the spring of 2009 has shown that the unique features of this new *Viburnum* plant are stable and reproduced true to type in successive generations of asexual reproduction.

SUMMARY OF THE INVENTION

Plants of the new *Viburnum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Spiro'. These characteristics in combination distinguish 'Spiro' as a new and distinct *Viburnum* plant:

1. Upright and somewhat outwardly spreading plant habit.
2. Vigorous growth habit.

3. Freely branching habit.
4. Red purple-colored flower buds.
5. Numerous strongly fragrant light pink to white-colored flowers.
6. Good garden performance.

Plants of the new *Viburnum* can be compared to plants of the female parent selection. Plants of the new *Viburnum* differ from plants of the female parent selection in the following characteristics:

1. Plants of the new *Viburnum* are more vigorous than plants of the female parent selection.
2. Flower buds of plants of the new *Viburnum* are darker in color than flower buds of plants of the female parent selection.
3. Flowers of plants of the new *Viburnum* are more fragrant than flowers of plants of the female parent selection.

Plants of the new *Viburnum* can be compared to plants of the *Viburnum carlesii* 'Compactum', not patented. Plants of the new *Viburnum* differ from plants of 'Compactum' in the following characteristics:

1. Plants of the new *Viburnum* are not as compact as plants of 'Compactum'.
2. Plants of the new *Viburnum* are faster growing than plants of 'Compactum'.
3. Flower buds of plants of the new *Viburnum* are darker in color than flower buds of plants of 'Compactum'.
4. Flowers of plants of the new *Viburnum* are more fragrant than flowers of plants of 'Compactum'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical plant of 'Spiro' grown in an outdoor nursery.

The photograph on the second sheet is a close-up view of a developing inflorescence of 'Spiro'.

DETAILED BOTANICAL DESCRIPTION

The aforementioned photographs and following observations, measurements and values describe plants of the new *Viburnum* grown during the spring in ground beds in an outdoor nursery in Grand Haven, Mich. and under cultural practices which closely approximate commercial *Viburnum* production. Plants were one year old when the photographs and the description were taken. In the description, color references are made to The Royal Horticultural Society Colour Chart, 1995 Edition, except where general terms of ordinary dictionary significance are used.

Botanical classification: *Viburnum carlesii* 'Spiro'.

Parentage:

*Female, or seed, parent*.—Unnamed selection of *Viburnum carlesii*, not patented.

*Male, or pollen, parent*.—Unknown selection of *Viburnum carlesii*, not patented.

Propagation:

*Type*.—By softwood cuttings.

*Time to initiate roots, summer*.—About 20 days at 25° C.

*Time to produce a rooted young plant, summer*.—About three months at 25° C.

*Root description*.—Fine to thick, fibrous.

*Rooting habit*.—Freely branching; dense.

Plant description:

*Plant and growth habit*.—Deciduous perennial shrub; upright and somewhat outwardly spreading plant habit; vigorous growth habit.

*Branching habit*.—Freely branching habit with numerous primary lateral branches; pinching (removal of terminal apices) will enhance lateral branch development.

*Plant height*.—About 1.4 meters.

*Plant diameter* (*area of spread*).—About 1 meter.

Lateral branch description:

*Length*.—About 27 cm.

*Diameter*.—About 5 mm.

*Internode length*.—About 10 cm.

*Texture*.—Developing stems, pubescent; developed stems, smooth, glabrous.

*Strength*.—Strong.

*Aspect*.—About 20° to 40° from vertical.

*Color, developing*.—Close to 197B.

*Color, developed*.—Close to 197A.

Foliage description:

*Arrangement*.—Opposite, simple.

*Length*.—About 11 cm.

*Width*.—About 7 cm.

*Shape*.—Ovate.

*Apex*.—Acute.

*Base*.—Obtuse.

*Margin*.—Serrate.

*Texture, upper and lower surfaces*.—Pubescent.

*Venation pattern*.—Pinnate.

*Color*.—Developing leaves, upper surface: Close to 137B. Developing leaves, lower surface: Close to 138B. Fully expanded leaves, upper surface: Close to 137A; venation, close to 138B. Fully expanded leaves, lower surface: Close to 138B; venation, close to 138B.

*Petiole*.—Length: About 4 mm. Diameter: About 3 mm. Texture, upper and lower surfaces: Smooth, glabrous. Color, upper and lower surfaces: Close to 138B.

Flower description:

*Flower appearance and arrangement*.—Single salverform flowers arranged in terminal cymes; freely flowering habit with usually about 61 flowers per inflorescence; flowers face upright to outwardly.

*Natural flowering season*.—Continuous flowering from the late spring to early summer in Grand Haven, Mich.; flowers last about four to six weeks on the plant and about two to three weeks as a cut flower; flowers not persistent.

*Fragrance*.—Strongly fragrant; sweet, pleasant.

*Inflorescence height*.—About 7 cm.

*Inflorescence diameter*.—About 8 cm.

*Flower diameter*.—About 2 cm.

*Flower length* (*height*).—About 1.5 cm.

*Flower bud*.—Length: About 1 cm. Diameter: About 4 mm. Shape: Club-shaped. Color: Close to 58A.

*Petals*.—Quantity per flower: Single whorl of five. Length: About 7 mm. Width: About 5 mm. Lobe shape: Rounded. Apex: Obtuse. Margin: Entire, undulate. Texture, upper and lower surfaces: Smooth, glabrous. Color: When opening, upper and lower surfaces: Close to 66D. Fully opened, upper surface: Close to 155C tinged with close to 73D; color becoming closer to 155D with development. Fully opened, lower surface: Close to 66D and 73D.

*Sepals*.—Quantity per flower: Two. Length: About 3 mm to 4 mm. Width: About 2 mm. Shape: Lanceolate. Apex: Acute. Margin: Entire. Texture, upper and lower surfaces: Smooth, glabrous. Color: When opening, upper and lower surfaces: Close to 143B. Fully opened, upper and lower surfaces: Close to 143B.

*Peduncles*.—Length: About 2 cm. Diameter: About 3 mm. Strength: Strong. Texture: Pubescent. Color: Close to 138C.

*Pedicels*.—Length: About 5 mm. Diameter: About 2 mm. Strength: Strong. Texture: Pubescent. Color: Close to 138C.

*Reproductive organs*.—Androecium: Quantity per flower: About five. Anther shape: Oblong. Anther size: About 1 mm by 0.3 mm. Anther color: Close to 138B. Amount of pollen: Scarce. Pollen color: Close to 138D. Gynoecium: Quantity per flower: One. Pistil length: About 1 mm. Style length: About 0.5 mm. Style color: Close to 138D. Stigma shape: Three-parted, flat. Stigma color: Close to 177A. Ovary color: Close to 178B.

*Seeds and fruits*.—Seed and fruit development have not been observed on plants of the new *Viburnum*.

Garden performance: Plants of the new *Viburnum* have been observed to have good garden performance and to tolerate rain, wind and temperatures ranging from about −15° C. to about 35° C.

Pathogen & pest resistance: Plants of the new *Viburnum* have not been observed to be resistant to pathogens and pests common to *Viburnum* plants.

It is claimed:

1. A new and distinct *Viburnum* plant named 'Spiro' as illustrated and described.

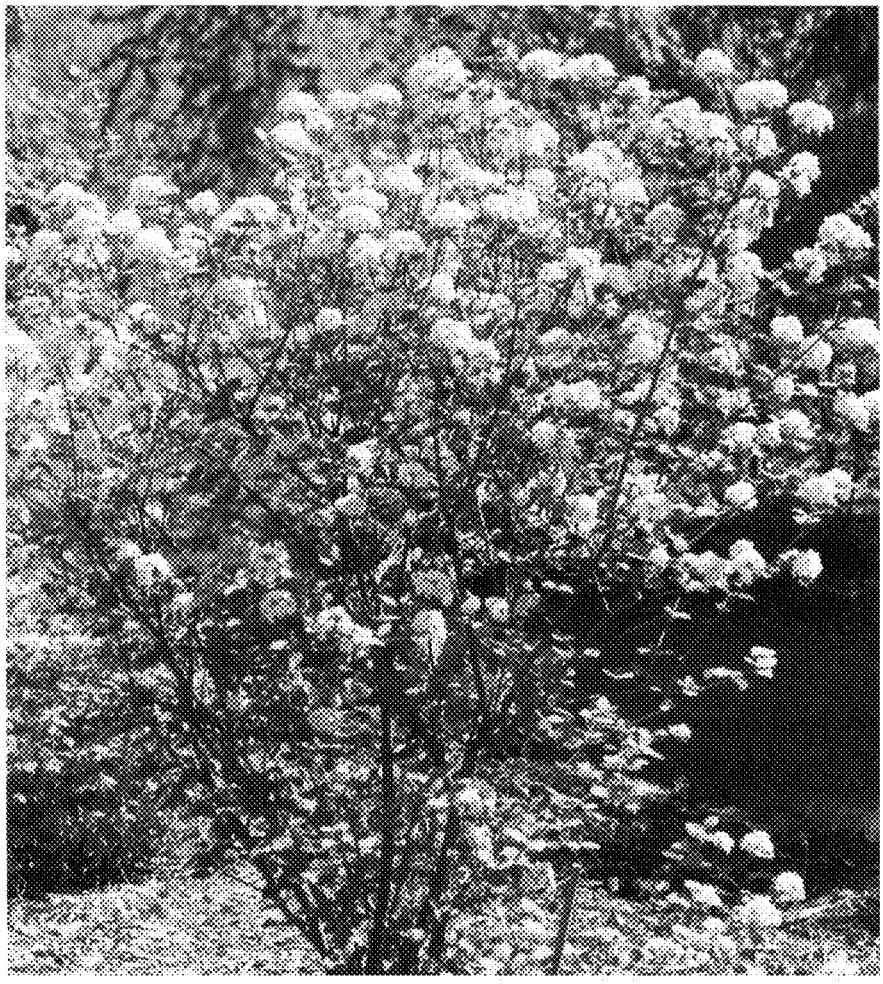

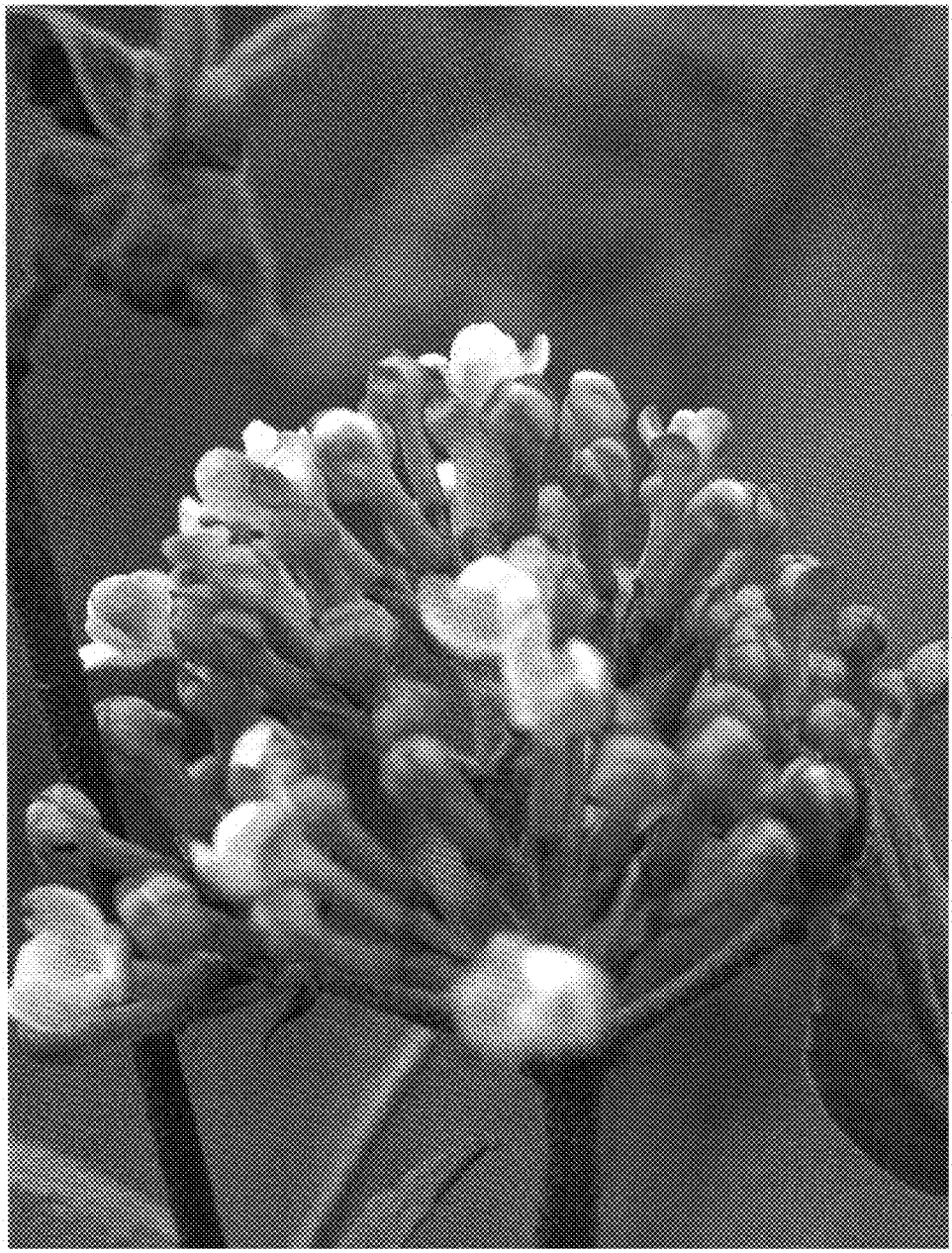

* * * * *